United States Patent [19]

Grollier et al.

[11] 4,425,132

[45] Jan. 10, 1984

[54] TWO-STAGE PROCESS FOR DYEING KERATIN FIBRES

[75] Inventors: Jean F. Grollier; Chantal Fourcadier, both of Paris, France

[73] Assignee: L'Oreal, Paris, France

[21] Appl. No.: 27,381

[22] Filed: Apr. 5, 1979

[30] Foreign Application Priority Data

Apr. 6, 1978 [FR] France ................................ 78 10277

[51] Int. Cl.³ .......................... A61K 7/13; A61K 9/12; D06P 3/14
[52] U.S. Cl. ........................................... 8/405; 8/406; 8/501; 424/47; 424/70
[58] Field of Search ........................... 8/501, 405, 406; 424/47

[56] References Cited

U.S. PATENT DOCUMENTS

| | | | |
|---|---|---|---|
| 2,085,809 | 6/1948 | Lehmann et al. | 8/406 |
| 3,582,253 | 6/1971 | Berth et al. | 8/406 |

FOREIGN PATENT DOCUMENTS

| | | | |
|---|---|---|---|
| 1959670 | 11/1969 | Fed. Rep. of Germany | 8/405 |
| 1124391 | 6/1956 | France | 8/405 |
| 1124392 | 6/1956 | France | 8/405 |
| 1163540 | 4/1958 | France | 8/405 |
| 1164951 | 5/1958 | France | 8/405 |
| 1166172 | 6/1958 | France | 8/405 |
| 2337784 | 8/1977 | France | 8/405 |
| 1234323 | 6/1971 | United Kingdom | 8/406 |
| 1290668 | 9/1972 | United Kingdom | 8/406 |
| 1294500 | 10/1972 | United Kingdom | 8/405 |
| 1326356 | 8/1973 | United Kingdom | 8/406 |

*Primary Examiner*—Dale R. Ore
*Attorney, Agent, or Firm*—Fleit, Jacobson, Cohn & Price

[57] ABSTRACT

A two-stage process for dyeing keratin fibres, especially human hair, is described which involves treating the fibres with a first composition at a first pH and subsequently, without rinsing, treating the fibres with a second composition at a second pH, at least one of the compositions containing a dyestuff for the fibres, and the second pH being different from the first pH so as to modify the effect of at least one active ingredient on the fibres.

31 Claims, No Drawings

TWO-STAGE PROCESS FOR DYEING KERATIN FIBRES

DESCRIPTION

The present invention relates to a process for dyeing keratin fibres and in particular hair.

It is well known to colour keratin fibres, and in particular human hair, with oxidisable dyestuffs or direct dyestuffs.

Oxidisable dyestuffs are used herein to mean so-called oxidative dyestuffs, diphenylamines and dyestuffs for rapid oxidation.

Aromatic compounds of the diamine, aminophenol or phenol type are referred to as oxidative dyestuffs. These compounds, which are not in themselves dyestuffs, are converted into dyestuffs by a process of oxidative condensation in the air or in the presence of an oxidising agent.

Amongst these oxidative dyestuffs, there may be distinguished, on the one hand, the oxidative dyestuff precursors of the para type, which are usually diamines or aminophenols in which the functional groups are located in the para position relative to one another, and the oxidative dyestuff precursors of the ortho type, which are usually diamines or aminophenols in which the functional groups are located in the ortho position relative to one another, and, on the other hand, modifying compounds or couplers which are so-called "meta derivatives," generally meta-diamines, m-aminophenols, m-diphenols as well as phenols.

This colouring of keratin fibres is most frequently carried out in a single step by applying the dyeing composition together with a cosmetic carrier, optionally containing oxidising agents depending on the nature of the dyestuff used.

Numerous cosmetically acceptable dyestuffs are also known which are of value by virtue of the colourations which they make it possible to achieve, their adhesion to the fibres and also their harmlessness; however, some of these dyestuffs cannot be used employing the customary hair-dyeing processes, either because they are unstable, or because they are sparingly soluble, or because they are cosmetically inactive under the usual hair-dyeing conditions because of the presence of certain ingredients such as acids bases, oxidising agents or reducing agents.

In order to be able to use these valuable compounds, it is necessary to apply them under special conditions such as in a cosmetic carrier which is suited to their solubility, stability and efficiency characteristics. However, these conditions are frequently different from those required for the other dyestuffs, with the result that it has hitherto been virtually impossible to combine the action of the dyestuffs acting under usual hair-treatment conditions with the action of those dyestuffs requiring these special conditions.

A few two-stage treatments are known, for example applying to the hair, in a first stage, an oxidative base in an ammoniacal medium, and, in a second stage, a coupler in an ammoniacal medium, which is mixed with an oxidising agent on the hair treated in this way; the treatment with the coupler is preceded by rinsing the head of hair which has been treated with the oxidative base beforehand.

However, such treatments do not make it possible to overcome the various abovementioned disadvantages associated with the stability, solubility and activity of these dyestuffs, or to combine the action of stable, soluble or active dyestuffs under different conditions.

The intermediate rinsing stage in practice causes removal of some of the compounds because the fixing of these compounds to the hair under the normal treatment conditions is difficult to achieve completely.

Finally, it can be desirable, in certain cases, to improve the diffusion of the dyestuffs into the hair and the fixing of the dyestuffs to the hair by raising the temperature.

We have now discovered, according to the present invention, a process for the treatment of keratin fibres, and in particular hair, which makes it possible to reduce or overcome the abovementioned disadvantages and to exploit, as far as possible, the characteristics and the properties of dyestuffs for keratin fibres and in particular for hair. In effect, we have discovered, inter alia, that it is possible to combine the action of different types of dyestuffs, such as direct dyestuffs and oxidative dyestuffs, which hitherto, when used in combination, have not given totally satisfactory results under the conditions of application either of the oxidative dyestuffs or of the direct dyestuffs.

The process according to the present invention also makes it possible to use couplers which do not couple, or couple very slightly, under the normal use conditions of oxidative dyes.

Finally, it is possible to cause the precipitation of the dyestuffs after their application to the hair.

Depending on the nature of the compounds present in the compositions applied in two stages to the hair, the two-stage process according to this invention can modify the consistency or the form of the composition resulting from the mixing of these compounds on the hair.

The two-stage process, according to the present invention, for dyeing keratin fibres, and in particular hair, is essentially characterised in that, in a first stage, the fibres are treated with a first composition which is at a first pH and contains a first agent for treating these fibres, and in that, in a second stage and before any rinsing, the fibres which have undergone the first treatment are treated with a second composition which is at a second pH and contains a second agent for treating the said fibres, the second pH being chosen so as to modify the pH of the combination of the two compositions kept on the fibres, for the purpose of assisting and/or modifying the action of the agents present in at least one of the said compositions on the keratin fibres, and at least one of these compositions containing one or more dyestuffs for the said fibres.

According to the invention, the pH of one of the compositions is basic and is preferably above 7 and up to 13, whereas the pH of the other composition is less than 8 and is preferably acid and is at least 1 but less than 7.

According to an advantageous embodiment of the invention, the first composition contains at least one alkalising agent present in an amount which is sufficient to give a pH above 7 but not exceeding 13, and the second composition, which has a pH from 1 to 8, contains at least one dyestuff for keratin fibres and in particular for human hair.

The alkalising agent which may be used in the first composition is an organic or inorganic base and is preferably sodium hydroxide, ammonia, potassium hydroxide, piperidine, an alkylamine, such as mono-, di- or tri-methylamine, mono-, di- or tri-ethylamine, mono-, di- or tri-propylamine, mono-, di- or tri-butylamine, mono-, di- or tri-isopropylamine, isobutylamine, tert.-butylamine, an amylamine, myristylamine or laurylamine, ethylenediamine, an alkanolamine, such as mono-, di- or tri-ethanolamine, mono-, di- or tri-propanolamine, mono-, di- or tri-isopropanolamine or 2-amino-2-methylpropanol, 2-amino-2-methylpropane-1,3-diol, an alkylalkanolamine or sodium carbonate potassium carbonate or ammonium carbonate.

This first composition can optionally contain dyestuffs for keratin fibres, and in particular for hair, which are stable under these conditions, such as oxidative dyestuffs, direct dyestuffs and diphenylamines.

According to a preferred embodiment of the invention, the first composition contains, in addition to the abovementioned alkalising agent, at least one oxidative dyestuff precursor of the para type and, more particularly, a compound corresponding to the formula:

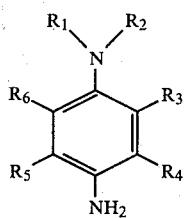
(I)

in which: $R_1$ and $R_2$ independently of one another denote hydrogen, phenyl, furfuryl, tetrahydrofurfuryl or a linear or branched alkyl group which can be chain-terminated by a substituent such as hydroxyl, alkoxy, amino (it being possible for the amino group to be primary, secondary or tertiary or to form part of a heterocyclic ring such as piperidino or morpholino), acylamino, alkyl- or aryl-sulphonylamino, carbalkoxyamino, ureido, carboxyl, carbamyl (in which the nitrogen atom can carry one or two substituents), sulpho or sulphonamido (in which the nitrogen atom can carry one or two substituents), it being possible for this alkyl group to be interrupted by one or more hetero-atoms, such as oxygen or nitrogen, and to carry other hydroxyl or amino groups; $R_1$ and $R_2$ can also form, together with the nitrogen atom to which they are attached, a heterocyclic ring such as piperidino or morpholino; and $R_3$, $R_4$, $R_5$ and $R_6$ independently of one another denote hydrogen, halogen, linear or branched alkyl which is optionally substituted by one or more OH, amino or alkoxy groups, or a group OZ, Z denoting alkyl, hydroxyalkyl, alkoxyalkyl, acylaminoalkyl, carbalkoxyaminoalkyl, mesylaminoalkyl, ureidoalkyl, aminoalkyl or mono- or di-alkylaminoalkyl, the alkyl radicals containing 1 to 6 carbon atoms, with the proviso that, if $R_2$ denotes phenyl, $R_1$, $R_3$, $R_4$, $R_5$ and $R_6$ denote hydrogen, and that, if $R_1$ and $R_2$ are both different from hydrogen, $R_3$ and $R_6$ denote hydrogen; and also the organic or inorganic acid salts of these bases, such as the hydrobromide, hydrochloride, sulphate, acetate and tartrate.

Amongst the compounds corresponding to the formula (I), there may be mentioned: para-phenylenediamine, para-toluylenediamine, methoxy-para-phenylenediamine, chloro-para-phenylenediamine, 2,6-dimethyl-para-phenylenediamine, 2,5-dimethyl-para-phenylenediamine, 4-aminodiphenylamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N-mono- and N,N-di-($\beta$-hydroxyethyl)-para-phenylenediamine, 3-methyl-4-amino-N,N-di-($\beta$-hydroxyethyl)-aniline, 3-chloro-4-amino-N,N-di-($\beta$-hydroxyethyl)-aniline, 4-amino-N-ethyl-N-carbamylmethylaniline, 4-amino-N-ethyl-N-($\beta$-morpholinoethyl)-aniline, 3-methyl-4-amino-N-ethyl-N-($\beta$-morpholinoethyl)-aniline, 4-amino-N-acetylaminoethylaniline, 4-amino-N-ethyl-N-acetylaminoethylaniline, 3-methyl-4-amino-N-ethyl-N-acetylaminoethylaniline, 4-amino-N-ethyl-N-($\beta$-mesylaminoethyl)-aniline, 3-methyl-4-amino-N-ethyl-N-($\beta$-mesylaminoethyl)-aniline, 4-amino-N-ethyl-N-($\beta$-sulphoethyl)-aniline, 3-methyl-4-amino-N-ethyl-N-($\beta$-sulphoethyl)-aniline, N-(4'-aminophenyl)-morpholine, N-(4'-aminophenyl)-piperidine, 4-amino-N-ethyl-N-piperidinoethylaniline, 3-methyl-4-amino-N-methylaniline, 2-chloro-4-amino-N-ethyl-N-sulphonamidomethylaniline, 2-chloro-4-amino-N-ethylaniline, 2-methyl-4-amino-N-($\beta$-hydroxyethyl)-aniline, 2,5-diaminophenoxyethanol, 4-($\beta$-methoxyethyl)-aminoaniline, N-methyl-para-phenylenediamine, 4-amino-N-($\beta$-hydroxyethyl)-N-($\beta$-mesylaminoethyl)-aniline, 4-amino-N-[$\beta$-($\beta'$-hydroxyethoxy)-ethyl]-aniline, 2-N-($\beta$-hydroxyethyl)-amino-5-aminophenoxyethanol, 4-N-(tetrahydrofurfuryl)-aminoaniline and 4-N-(furfuryl)-aminoaniline.

Other oxidative dyestuff precursors of the "para" type which can be used according to the invention include para-aminophenols, such as para-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol and N-methyl-para-aminophenol, heterocyclic precursors derived from pyridine, such as 2,5-diaminopyridine, 2-dimethylamino-5-aminopyridine, 2-diethylamino-5-aminopyridine or alternatively 2-methyl-6-aminobenzomorpholine and 5-aminoindole, and bis-condensed precursors such as the N,N'-diarylalkylenediamines in which the aryl groups are substituted in the para position by a OH or amino group optionally substituted by an alkyl group and can be substituted on the nucleus by an alkyl radical or a halogen atom, and in which the alkylene group can be interrupted by a hetero-atom, such as O or N, and is optionally substituted by OH, it being possible for the nitrogen atoms of the alkylenediamine group to be substituted by an alkyl, hydroxyalkyl or aminoalkyl group.

Compounds of this type are described, inter alia, in French Pat. No. 2,016,123.

These compositions can also contain oxidative dyestuff precursors of the ortho type, such as ortho-phenylenediamine, ortho-aminophenol or derivatives thereof substituted on the nitrogen atom by one or more alkyl or hydroxyalkyl groups.

The couplers which can be used are stable couplers which develop intense colourations under conditions which are such that the pH is from 7 to 13.

These couplers are in general, monophenol derivatives, meta-diphenols, meta-aminophenols and meta-diamines, which can be represented by the general formula:

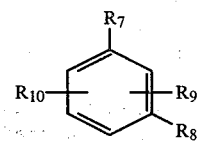
(II)

in which:

when formula (II) represents a phenol coupler, one of the substituents $R_7$ or $R_8$ denotes OH and the other substituents (R groups), which are different from OH, denote hydrogen, alkyl, alkoxy or halogen, one of the para or ortho positions, relative to the OH group, being free or substituted by halogen or alkoxy;

when formula (II) represents a m-diphenol, $R_7$ and $R_8$ denote OH, it being possible for $R_9$ and $R_{10}$ to denote hydrogen or an alkyl, alkoxy or halogen group;

when formula (II) represents a m-aminophenol, one of the groups $R_7$ or $R_8$ denotes OH and the other group represents

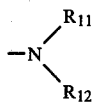

in which: $R_{11}$ and $R_{12}$, which are identical or different, denote hydrogen, linear or branched alkyl optionally chain-terminated by a OH, alkoxy or optionally mono- or di-substituted amino group, or a heterocyclic ring such as piperidino or morpholino, it being possible for the alkyl group to contain other hydroxy or amino substituents, or chain ether groups, such that if one of the substituents $R_{11}$ or $R_{12}$ denotes acyl, carbamyl, carbamylalkyl in which the nitrogen atom is optionally mono- or di-substituted, alkyl- or aryl-sulphonyl, sulphonamidoalkyl in which the nitrogen atom is optionally mono- or di-substituted, carbethoxy or mesylaminoalkyl, the other substituent denotes hydrogen; $R_9$ and $R_{10}$, which are identical or different, represent hydrogen, halogen, linear or branched alkyl or a group $OZ_1$, $Z_1$ representing alkyl, or alkylene forming with the nitrogen atom $R_7$ or $R_8$ a morpholino ring; and when formula (II) denotes a m-diamine, $R_7$ and $R_8$ both denote a group

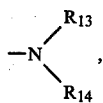

each $R_{13}$ and each $R_{14}$ being the same or different, $R_{13}$ and $R_{14}$, which are identical or different, denoting hydrogen or linear or branched alkyl which is optionally substituted by OH, amino, alkoxy, carbamyl or alkyl- or aryl-sulphonylamino, it being possible for one of the groups $R_{13}$ or $R_{14}$ to denote an alkylsulphonyl, acyl or carbamylalkyl group if the other denotes hydrogen; $R_9$ and $R_{10}$, which are identical or different, denote hydrogen, halogen, linear or branched alkyl or $OZ_1$, $Z_2$ denoting alkyl, hydroxyalkyl, alkoxyalkyl, arylaminoalkyl, mesylaminoalkyl, ureidoalkyl or carbalkoxyalkyl, or alkylene, forming with the nitrogen atom of $R_7$ or $R_8$ a morpholino ring, and organic or inorganic acid salts thereof such as the hydrochloride, hydrobromide, sulphate, acetate and tartrate.

In the formulae of the abovementioned oxidisable dyestuffs, the alkyl groups preferably denote groups having from 1 to 6 carbon atoms, such as methyl, ethyl, propyl, isopropyl, n-butyl and i-butyl groups, alkoxy denotes a group preferably having 1 to 6 carbon atoms, such as methoxy, ethoxy and propoxy, acyl generally denotes a derivative of a carboxylic acid having 1 to 7 carbon atoms, halogen denotes chlorine, bromine and fluorine, and the substituents of the nitrogen atom are preferably alkyl groups having from 1 to 6 carbon atoms.

Amongst the couplers corresponding to the general formula II, there may be mentioned, in particular, resorcinols, such as resorcinol, 2-methylresorcinol and 4-chlororesorcinol, meta-aminophenol, 2,4-diaminoanisole, 2-methyl-5-ureidophenol, 2,6-dimethyl-3-aminophenol, 2-methyl-5-acetylaminophenol, 2,6-dimethyl-5-acetylaminophenol, 3-amino-4-methoxyphenol, 2-methyl-5-N-(β-hydroxyethyl)-aminophenol, meta-phenylenediamine, meta-toluylenediamine, N-methyl-meta-aminophenol, 6-methyl-3-aminophenol, 2,4-diaminophenoxyethanol, 3-N-dimethylaminophenol, 6-methyl-3-N-(β-mesylaminoethyl)-aminophenol, 6-methyl-3-N-carbamylmethylaminophenol, 3-N-carbamylmethylaminophenol and 2-N-(β-hydroxyethyl)-amino-4-aminophenoxyethanol and salts of these compounds.

Other couplers which can be used in the process according to the invention include, naphthol, heterocyclic compounds, and, in particular, morpholine derivatives such as 6-hydroxybenzomorpholine and 6-aminobenzomorpholine, pyridine derivatives, such as 2,6-diaminopyridine, pyrazolones and diketone compounds and their salts.

The diphenylamines which can be used in the process according to the invention are diphenylamines in which the two benzene nuclei are substituted in the 4- and 4'-position by 2 groups such as hydroxyl and/or NR'R" in which R' and R" independently (or simultaneously) denote: hydrogen, alkyl or hydroxyalkyl, and R" can additionally denote carbamylalkyl, mesylaminoalkyl, acylaminoalkyl, sulphoalkyl, piperidinoalkyl or morpholinoalkyl, if R' denotes H or alkyl. The radicals R' and R" can form, together with the nitrogen atom to which they are attached, a piperidino or morpholino heterocyclic ring. The other positions of the 2 benzene nuclei can be occupied by one or more groups such as alkyl or alkoxy in which the alkyl radical can be attached to a primary or secondary amine group in the 4- or 4'-position, thus forming a heterocyclic ring, a halogen atom, or a ureido or amino radical which is optionally substituted by a hydroxyalkyl, carbamylalkyl, mesylaminoalkyl, acyl or carbalkoxy group.

These diphenylamines can be used in the form of their salts such as the sulphate, hydrobromide, hydrochloride, acetate or tartrate.

These diphenylamines are described in, for example, French Pat. Nos. 1,222,700, 2,056,799, 2,174,473, 2,145,724, 2,262,023, 2,262,024 and 2,261,750 and Published Application No. 75/05,503, which have been included by way of reference.

The second composition, which generally has an acid pH, preferably contains organic or inorganic acids such as hydrochloric acid, sulphuric acid, boric acid, phosphoric acid, formic acid, acetic acid, propionic acid, butyric acid, pentanoic acid, hexanoic acid, heptanoic acid, octanoic acid, cinnamic acid, lactic acid, glycolic acid, caproic acid, valeric acid, stearic acid, oleic acid, ricinoleic acid, linoleic acid, palmitic acid, lauric acid and myristic acid, diacids, such as oxalic acid, malonic acid, succinic acid, glutamic acid, adipic acid, maleic acid, fumaric acid, tartaric acid and malic acid, and triacids such as citric acid.

It is self-evident that the pH can be adjusted by the dyestuffs themselves, since these can be acidic.

This second composition can contain, in particular, direct dyestuffs and, according to a preferred embodiment of the invention, dyestuffs which are unstable or insoluble in an alkaline medium, are unstable or inactive, as regards dyeing, in an oxidising alkaline medium, possess a low affinity for keratin fibres at a strongly alkaline pH, or are unstable in the presence of the reducing agents which are required for storing the compositions in which oxidative dyestuffs are present.

These direct dyestuffs are, in particular nitrobenzene dyestuffs, anthraquinone dyestuffs, triphenylmethane dyestuffs, azo dyestuffs, metallised dyestuffs, xanthene dyestuffs and acridine dyestuffs and also polymeric dyestuffs.

Amongst these dyestuffs, there may be mentioned: nitrobenzene derivatives, such as 1,3-dihydroxy-2-nitrobenzene, 6-methyl-3-amino-2-nitrophenol, 6-chloro-3-amino-2-nitrophenol and 6-methyl-3-N-($\beta$-hydroxyethyl)-amino-2-nitrophenol and also other compounds of this type which are insufficiently stable during storage in an alkaline medium, such as the dyestuff referred to in the Color Index as Acid Red 277, and anthraquinone dyestuffs such as those of the general formula:

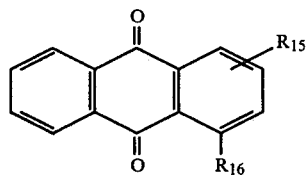
(III)

in which: $R_{15}$ denotes —OH, —NHR$_{17}$ or —NH—(CH$_2$)$_x$—NR$_8$R$_{17}$, x being from 1 to 4, and R$_{16}$ denotes H, OH, NHR$_{17}$ and R$_{15}$, R$_{17}$ or R$_{18}$ independently of one another denote hydrogen or lower alkyl (having 1 to 6 carbon atoms), such as methyl, or ethyl.

Amongst these dyestuffs, those which are more particularly preferred are: 2-N-($\beta$-aminoethyl)-aminoanthraquinone, 1-N-($\gamma$-aminopropyl)-aminoanthraquinone and 1-N-methylamino-4-N'-($\gamma$-aminopropyl)-aminoanthraquinone, which are sparingly soluble in a strongly alkaline medium.

Polymeric dyestuffs can be obtained, in particular, by grafting one or more anthraquinone dyestuffs or nitro benzene dyestuffs, in molar amounts from 2 and 90%, onto products resulting from the polycondensation of adipic acid with diethylenetriamine. They correspond, in particular, to the general formula:

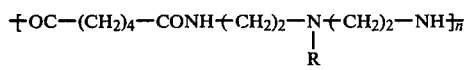

in which R denotes H or, in at least one case, an anthraquinone dyestuff and n is from 2 to 20, and are unstable or inactive, as regards dyeing, in an alkaline oxidising medium.

Other dyestuffs which exhibit disadvantages and give remarkable results in accordance with the invention include acidic, basic or disperse direct dyestuffs such as those referred to in the Color Index under the following designations: Acid Black 61 and 140, Acid Blue 166, 151, 183, 199 and 209, Acid Brown 48 and 252, Acid Green 65 and 91, Acid Orange 88, Acid Red 225, 252 and 278, Acid Violet 95, Disperse Blue 7 and 58, Disperse Red 15, Disperse Violet 4, Basic Black 1, Basic Blue 26, 18 and 54, Basic Green 6, Basic Orange 21, 27 and 22, Basic Red 13, Basic Violet 7 and 1 and Basic Yellow 11, 12, 17, 18, 19, 20, 21 and 22.

Other direct dyestuffs which can be used and which possess a better affinity for keratin fibers at neutral or acid pH include 4-amino-3-nitrophenol, 3-nitro-4-N-($\beta$-hydroxyethyl)-aminophenol, 2-N-($\beta$-hydroxyethyl)-amino-5-nitroanisole and 3-nitro-4-N'-methylamino-N,N-di-($\beta$-hydroxyethyl)-aniline and also the dyestuffs included in the Color Index under the following designations: Acid Black 58, 107, 2, 31 and 139, Acid Blue 20 and 168, Acid Brown 227, Acid Green 66, Acid Orange 24, Acid Red 35, 251 and 253, Acid Violet 43 and 70, Disperse Black 5, Disperse Blue 2 and 3, Disperse Orange 18 and 5, Disperse Red 12, 17 and 11, Disperse Yellow 3, Basic Brown 1 and 4, Basic Orange 14 and 28, Basic Red 29, Basic Violet 3, 10 and 1 and Solvent Black 29.

The second composition can also contain couplers which couple less satisfactorily under the pH conditions of the first composition. These couplers correspond, in particular, to the formula

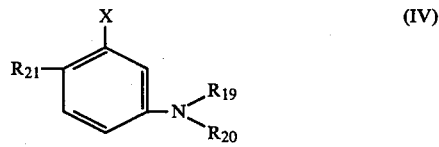
(IV)

in which: X denotes —OH, —NH$_2$ or —N(CH$_3$)$_2$, R$_{21}$ and R$_{19}$ independently denote H or a lower alkyl radical (having 1 to 4 carbon atoms), such as methyl or ethyl, and R$_{20}$ denotes —COCH$_3$, —CONH$_2$ or a lower alkyl radical having 1 to 4 carbon atoms, such as methyl or ethyl, or alternatively, to the formula:

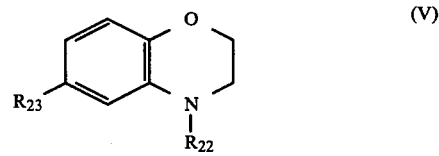
(V)

in which: R$_{22}$ denotes hydrogen, —COCH$_3$ or —CONH$_2$ and R$_{23}$ denotes OH or amino, as well as their organic or inorganic acid salts such as the hydrochloride, hydrobromide, sulphate, acetate and tartrate, and also 6-aminoindoline.

It has been found that, on using these dyestuffs in the process according to the invention, a better affinity of these dyestuffs for the fibres is achieved compared with the affinity which is found with a conventional application at a strongly alkaline pH and in a single step.

The process according to the invention also makes it possible to obtain good results when using, in the second composition, the following dyestuffs which are unstable in the presence of reducing agents required for storing compositions in which oxidative dyestuffs are present: 4-amino-3-nitrophenol, 3-nitro-4-N-($\beta$-hydroxyethyl)-aminophenol and 3-nitro-4-N'-methylamino-N,N-di-($\beta$-hydroxyethyl)-aniline.

According to an advantageous embodiment of the invention, the first composition can be mixed, just before use, with an oxidising composition containing, in particular, as an oxidising agent, hydrogen peroxide in an amount from 0.1 to 20% by weight.

According to another embodiment of the invention, the pH of the first composition is less than 8 and the pH of the second composition is adjusted so as to give the combination of the two compositions on the keratin fibres a pH of more than 8.

In this embodiment, the first composition can contain dyestuffs, such as oxidative dyestuffs and direct dyestuffs, and also diphenylamines. This embodiment is particularly advantageous in the case of oxidisable dyestuffs where their oxidation products are highly sterically hindered and which penetrate with difficulty into the fibre.

In this context, there may be mentioned the oxidative dyestuff precursors of the para type in which the amino group is secondary or tertiary and in which the nucleus is highly hindered, and, more particularly, the compounds corresponding to the formula I above in which, if $R_1$ and $R_2$ simultaneously denote hydrogen, at least two of the radicals $R_3$, $R_4$, $R_5$ and $R_6$ are different from hydrogen.

It is also possible to use so-called "rapid" oxidative dyestuffs which are polyhydroxybenzenes and polyhydroxynaphthalenes, such as pyrogallol, 1,2,4-trihydroxybenzene, 5-($\beta$-aminoethyl)-1,2,4-trihydroxybenzene, 1,3,5-trihydroxybenzene, 2,4,5-trihydroxytoluene and 1,4,5-trihydroxynaphthalene, polyaminobenzenes, such as 1,2,4-triaminobenzene, polyaminophenols, such as di- or tri-aminophenols, polyaminopolyhydroxybenzenes in which the amino groups are optionally substituted by an alkyl group, and polyhydroxy- or polyaminohydroxy-indoles, used preferably when a direct dyestuff or a para type precursor is present in the first composition.

These compositions can also contain diphenylamines of the type mentioned above.

Other dyestuffs which can be used in this case include direct dyestuffs such as nitro dyestuffs, anthraquinone, triphenylmethane, azo, metallised, xanthene and acridine derivatives and also the polymeric dyestuffs, such as those defined above.

If the compositions contain rapid oxidative dyestuffs, the pH should be kept at less than 8, and preferably less than 6, using the abovementioned acidifying agents.

In this case, the second composition applied to the hair contains an alkalising agent, such as those mentioned above, which is present in a sufficient amount to give the mixture a pH of more than 8, in order to develop the colouration on the hair. This composition can also contain dyestuffs which are stable under the specified pH conditions, such as oxidative dyestuffs which are less sterically hindered, for example of the para type.

If the first composition contains oxidative dyestuff, this procedure makes it possible to allow the oxidative base, for example, to penetrate into the hair and then to develop the colouration, optionally by means of a coupler, and under optimal pH conditions assisting the process of oxidative condensation of the oxidisable dyestuffs.

The basic pH can also result in the precipitation of the dyestuffs inside the keratin fibre, this being particularly advantageous in the case of direct dyestuffs such as anthraquinone dyestuffs.

The various acids or bases used according to the invention should naturally be present in the compositions in proportions which are acceptable from the cosmetic point of view, in general from 0.05 to 25% by weight and preferably from 0.2 to 10% by weight.

The oxidative dyestuff precursors of the para type, the couplers and also the other oxidisable dyestuffs are usually each present in amounts from 0.005 to 10% by weight and preferably from 0.01 to 5% by weight.

The direct dyestuffs are preferably present in amounts from 0.005 to 10% by weight, and, in particular, from 0.05 to 6% by weight.

The polymeric dyestuffs are suitably present in amounts from 0.5 to 10% by weight and preferably from 1 to 6% by weight.

The application time of the first composition is generally from 2 to 40 minutes, and preferably from 10 to 30 minutes, whereas the application time of the second composition is generally from 1 to 40 minutes and preferably from 5 to 30 minutes.

Following the application the keratin fibres are generally rinsed and optionally shampooed.

The various compositions used in carrying out the present invention can be in the form of, for example, aqueous, thickened, gelled or gellable compositions or creams, which composition can be packaged in an aerosol.

The gelled or gellable compositions can be obtained either from polyoxyethyleneated or polyglycerolated non-ionic compounds in the presence of solvents, or from soaps of liquid fatty acids, such as oleic acid or isostearic acid, in the presence of solvents in an aqueous vehicle.

The fatty acids are generally used to form the soaps at concentrations from 0.5 to 25% by weight.

The alkalising agents used to form the soaps are suitably sodium hydroxide, potassium hydroxide, ammonia, monoethanolamine, diethanolamine or triethanolamine or mixtures thereof.

Amongst the polyoxyethyleneated non-ionic compounds, there may be mentioned, in particular, polyoxyethyleneated nonylphenol containing 4 mols of ethylene oxide (per mole of phenol) and polyoxyethyleneated nonylphenol containing 9 mols of ethylene oxide.

These constituents are preferably present at concentrations from 5 to 60% by weight.

Amongst the polyglycerolated non-ionic compounds, there may be mentioned, in particular, polyglycerolated oleyl alcohol containing 2 mols of glycerol and polyglycerolated oleyl alcohol containing 4 mols of glycerol.

These constituents are preferably present at concentrations from 5 to 60% by weight.

Amongst the solvents which can be used by themselves, or in a mixture, there may be mentioned ethyl, isopropyl, butyl or benzyl alcohols, and glycols or glycol ethers, such as ethylene glycol monomethyl, monoethyl or monobutyl ether (methyl, ethyl and butyl cellosolve), propylene glycol, carbitol and butylcarbitol.

These constituents are preferably present at concentrations from 2 to 40% by weight.

All the specified concentrations are based on the total weight of the dyeing composition.

If the compositions are in the form of creams, their formulation is essentially based on soaps or fatty alcohols in the presence of emulsifying agents and in an aqueous vehicle.

The soaps can be formed from natural or synthetic fatty acids having from 12 to 18 carbon atoms, such as lauric acid, myristic acid, palmitic acid and stearic acid, and from alkalising agents such as sodium hydroxide, potassium hydroxide, ammonia, monoethanolamine, diethanolamine and triethanolamine. The creams preferably contain from 10 to 30% by weight of fatty acids.

The creams can also be formulated from natural or synthetic fatty alcohols having between 12 and 18 carbon atoms, in a mixture with emulsifying agents. Amongst these fatty alcohols, there may be mentioned, in particular, lauryl alcohol, alcohols derived from copra fatty acids, myristyl alcohol, cetyl alcohol, stearyl alcohol and hydroxystearyl alcohol. The concentration of fatty alcohols in the creams is generally 5 to 25% by weight.

The emulsifying agents which can be used in the composition include polyoxyethyleneated or polyglycerolated fatty alcohols such as polyoxyethyleneated oleyl alcohol containing from 10 to 30 mols of ethylene oxide, polyoxyethyleneated cetyl alcohol containing from 6 to 10 mols of ethylene oxide, polyoxyethyleneated lauryl alcohol containing 12 mols of ethylene oxide, oxyethyleneated cetyl/stearyl alcohol containing 10 or 15 mols of ethylene oxide, polyoxyethyleneated oleyl/cetyl alcohol containing 30 mols of ethylene oxide, polyoxyethyleneated stearyl alcohol containing 10, 15 or 20 mols of ethylene oxide, polyglycerolated oleyl alcohol containing 4 mols of glycerol and synthetic fatty alcohols which contain from 9 to 15 carbon atoms and are polyoxyethyleneated with 5 or 10 mols of ethylene oxide; polyoxyethyleneated castor oil can also be used. These non-ionic emulsifying agents are suitably present in the compositions in an amount of 1 to 25% by weight.

Other emulsifying agents which can be used include alkyl-sulphates which may or may not be oxethyleneated, such as sodium lauryl-sulphate, ammonium lauryl-sulphate, sodium cetyl-/stearyl-sulphate, triethanolamine cetyl-/stearyl-sulphate, monoethanolamine lauryl-sulphate or triethanolamine lauryl-sulphate, the sodium salt of the sulphate half-ester of oxyethyleneated lauryl alcohol containing, for example, 2.2 mols of ethylene oxide, and the monoethanolamine salt of the sulphate half-ester of oxyethyleneated lauryl alcohol containing, for example, 2.2 mols of ethylene oxide.

These constituents are preferably present in these compositions at a concentration of 1 to 15% by weight.

In addition to the soaps, the fatty alcohols and the emulsifying agents mentioned above, these creams can contain adjuvants, such as fatty amides, which are usually employed in compositions of this kind.

Fatty amides which are preferably used are mono- or di-ethanolamides of acids derived from copra, of lauric acid or of oleic acid; they are generally used at concentrations up to 10% by weight, relative to the total weight of the composition.

These compositions used in the process according to the invention can contain reducing agents such as sodium sulphite, sodium metabisulphite, sodium bisulphite and sodium dithionite, ascorbic acid, isoascorbic acid, homogentisic acid, 1-phenyl-3-methylpyrazol-5-one and mercaptans such as thiolactic acid and thioglycolic acid. The concentrations of these compounds is typically up to 1%.

The compositions can also contain solvents, thickeners, treating agents, sequestering agents, such as ethylenediaminetetraacetic acid, diethylenetriaminepentaacetic acid or their salts, perfumes, sun filters and preservatives for example.

Solvents can be added to the composition in order to solubilise the dyestuffs which are insufficiently soluble in water. In this case, the solvents which can be used may be the same as those indicated above for the composition of the gellable liquids.

Amongst the thickeners which can be used in these compositions, there may be mentioned sodium alginate, gum arabic, cellulose derivatives, such as methylcellulose, hydroxyethylcellulose, hydroxypropylcellulose, hydroxypropylmethylcellulose and carboxymethylcellulose, or carboxyvinylic polymers such as the "Carbopols."

These constituents are typically present in an amount from 0.5 to 5%. The treating agents which can be used in these compositions are mainly intended to improve the feel of the hair and to make the hair easier to comb out. They can be quaternary amines, such as trimethylcetylammonium bromide, cetylpyridinium chloride, stearyltrimethylammonium chloride, dilauryldimethylammonium chloride or distearyldimethylammonium chloride, used alone or as a mixture, or cationic polymers such as the quaternary derivatives of cellulose ether, for example JR 400 of Messrs. Union Carbide.

The concentration of treating agent is generally from 0.1 to 5% by weight.

The following Examples further illustrate the present invention.

In the following Examples, the tradenames used denote respectively:

Remcopal 334: polyoxyethyleneated nonylphenol containing 4 mols of ethylene oxide, sold by Messrs. Gerland.

Remcopal 349: polyoxyethyleneated nonylphenol containing 9 mols of ethylene oxide, sold by Messrs. Gerland.

Masquol DTPA: pentasodium salt of diethylenetriaminepentaacetic acid, sold by Messrs. Protex.

Polychol 5: oxyethyleneated lanoline fatty alcohol containing 5 mols of ethylene oxide, sold by Messrs. Croda Ltd.

Polychol 20: oxyethyleneated lanoline fatty alcohol containing 20 mols of ethylene oxide, sold by Messrs. Croda Ltd.

Cellosize WP 4400: hydroxyethylcellulose sold by Messrs. Carbide and Carbon.

Carbopol 934: crosslinked acrylic acid polymer sold by Messrs. Goodrich Chemicals.

Comperlan KD: diethanolamides of copra fatty acids, sold by Messrs. Dehydag.

Brij 76: stearyl alcohol containing 10 mols of ethylene oxide, sold by Messrs. Atlas Powder.

Cellosize WP 3: hydroxyethylcellulose sold by Messrs. Carbide and Carbon.

Polymer P 1: coloured polymer resulting from the condensation of 0.0052 mol of 1-($\gamma$-chloroacetylaminopropylamino)-anthraquinone, 0.0048 mol of 2-($\beta$-chloroacetylaminoethylamino)-anthraquinone and 0.0055 mol of 1-methylamino-4-($\gamma$-chloroacetylaminopropylamino)-anthraquinone with 9.65 g (0.0052 equivalent of basic nitrogen) of the polymer obtained by condensing equimolecular amounts of adipic acid and diethylenetriamine.

| OXIDISING COMPOSITIONS | |
|---|---|
| Composition 01: | |
| Polychol 5 | 3.3 g |
| Polychol 20 | 1.7 g |
| Stearyl alcohol | 5 g |
| Hydrogen peroxide of 100 volumes strength | 20 g |
| Phosphoric acid q.s.p. | pH 3 |
| Water q.s.p. | 100 g |
| Composition 02: | |
| Hydrogen peroxide of 100 volumes strength | 20 g |

| -continued | |
|---|---|
| OXIDISING COMPOSITIONS | |
| Phosphoric acid q.s.p. | pH 3 |
| Water q.s.p. | 100 g |
| Composition 03: | |
| Polychol 5 | 3.3 g |
| Polychol 20 | 1.7 g |
| Stearyl alcohol | 5 g |
| Hydrogen peroxide of 100 volumes strength | 2 g |
| Phosphoric acid q.s.p. | pH 3 |
| Water q.s.p. | 100 g |

In the following Examples, the mixing of the two parts of each composition on the head of hair can cause slight warming, depending on the nature and the concentration of the acidic and basic components.

EXAMPLE NO. 1

The following dyeing compositions are prepared:

| Composition $S_1$: | |
|---|---|
| Remcopal 334 | 22 g |
| Remcopal 349 | 22 g |
| Propylene glycol | 11 g |
| Absolute ethyl alcohol | 8 g |
| 35° Bé strength sodium bisulphite solution | 1 cc |
| Masquol DTPA | 2.5 g |
| 22° Bé strength ammonia solution | 10 cc |
| Water q.s.p. | 100 g |
| Composition $S_2$: | |
| Rouge Supracide 2 B (FMC) (C.I. Acid Red 35) | 5 g |
| Remcopal 334 | 20 g |
| Remcopal 349 | 20 g |
| Carbopol 934 | 1.25 g |
| Ethylene glycol distearate | 0.5 g |
| Propylene glycol | 6 g |
| Absolute ethyl alcohol | 8 g |
| Phosphoric acid (d = 1.71) | 0.6 g |
| Citric acid | 1 g |
| Water q.s.p. | 100 g |

7 g of the composition $S_1$, which has been mixed, before use, with an equal amount of the oxidising composition 01, are applied to a 1 g swatch of light chestnut hair.

This mixture has a pH of about 10.

After 15 minutes, 14 g of the composition $S_2$ are incorporated on the hair (the pH of the mixture is then 4) and the hair is then left for a further 15 minutes, after which the swatch is rinsed with water, shampooed and dried.

The hair is coloured pearlescent blond.

For comparison, 7 g of the oxidising composition 01, which has been mixed, before use, with 21 g of the following dyeing composition:

| Rouge Supracide 2 B (FMC) (C.I. Acid Red 35) | 3.4 g |
|---|---|
| Remcopal 334 | 15 g |
| Remcopal 349 | 15 g |
| Propylene glycol | 7.5 g |
| Absolute ethyl alcohol | 5.3 g |
| 35° Be strength sodium bisulphite solution | 1 cc |
| Masquol DTPA | 2.4 g |
| 22° Be strength ammonia solution | 6.5 cc |
| Water q.s.p. | 100 g | are applied to a swatch of light chestnut hair.

After 30 minutes, the swatch of hair is rinsed before shampooing and drying.

The swatch treated in this way is coloured blond but virtually no sheen is observed, even though the pearlescent dyestuff was used in the dyebath at the same concentration as previously and its contact time with the hair was doubled.

EXAMPLE NO. 2

The following dyeing composition is prepared:

| Composition $S_3$: | |
|---|---|
| Polymeric dyestuff $P_1$ | 1.5 g |
| Cellosize WP 4400 | 2 g |
| Maleic acid | 2 g |
| Water q.s.p. | 100 g |

7 g of the composition $S_1$ defined in Example 1, which has been mixed, before use, with an equal amount of the oxidising composition 01, are applied to a swatch of light chestnut hair.

This mixture has a pH of about 10.

After 15 minutes, 7 g of the composition $S_3$ are incorporated with careful massaging.

The dyebath present on the hair then possesses a pH of 6.5 and the hair is left for a further 15 minutes before rinsing with warm water and shampooing.

After drying, the hair is coloured natural ashen blond and has a pleasant feel.

EXAMPLE NO. 3

The following dyeing compositions are prepared:

| Composition $S_4$: | |
|---|---|
| 22° Bé strength ammonia solution | 10 cm³ |
| Ethylenediaminetetraacetic acid | 0.2 g |
| Water q.s.p. | 100 g |
| Composition $S_5$: | |
| 1-N—Methylamino-4-N—($\gamma$-aminopropyl)-aminoanthraquinone hydrochloride | 1 g |
| Hydrochloric acid (d = 1.18) | 8.5 cm³ |
| Water q.s.p. | 100 g |

5 g of the composition $S_4$, which has been mixed, before use, with 5 g of the oxidising composition 02, are applied to a swatch of deep blond hair.

This mixture has a pH of 10.5.

After 15 minutes, 5 g of the composition $S_5$ are incorporated and the pH of the dyebath has then been lowered to 6.

The hair is left for a further 15 minutes and is rinsed with water before shampooing and drying the swatch which is dyed ashen light blond. The shading thus produced is more intense than in the case where an identical swatch is treated for the same time (30 minutes) in accordance with a usual process for lightening the colour of the hair with direct dyestuffs, that is to say using 10 g of a composition containing the same concentration of dyestuffs:

| 1-N—methylamino-4-N—($\gamma$-aminopropyl)-aminoanthraquinone hydrochloride | 0.5 g |
|---|---|
| Ethylenediaminetetraacetic acid | 0.2 g |
| 22° Bé strength ammonia solution | 10 cc |
| Water q.s.p. | 100 g | which is mixed, before use, with 5 g of the oxidising composition 02.

EXAMPLE NO. 4

The following dyeing compositions are prepared:

| Composition S<sub>6</sub>: | |
|---|---|
| Para-toluylenediamine | 0.32 g |
| Para-aminophenol | 0.25 g |
| Resorcinol | 0.25 g |
| Meta-aminophenol | 0.10 g |
| Remcopal 334 | 22 g |
| Remcopal 349 | 22 g |
| Propylene glycol | 11 g |
| Absolute ethyl alcohol | 8 g |
| 35° Bé strength sodium bisulphite solution | 1 cc |
| Masquol DTPA | 2.5 g |
| 1-Phenyl-3-methylpyrazol-5-one | 0.2 g |
| Hydroquinone | 0.2 g |
| 22° Bé strength ammonia solution | 10 cc |
| Water q.s.p. | 100 g |
| Composition $S_7$: | |
| 3-Nitro-4-N—(β-hydroxyethyl)-aminophenol | 1 g |
| Remcopal 334 | 20 g |
| Remcopal 349 | 20 g |
| Carbopol 934 | 1.25 g |
| Ethylene glycol distearate | 0.5 g |
| Propylene glycol | 6 g |
| Absolute ethyl alcohol | 8 g |
| Hydrochloric acid (d = 1.18) | 1.3 g |
| Citric acid | 1 g |
| Water q.s.p. | 100 g |

30 g of the composition $S_6$ are mixed with 30 g of the oxidising composition 02 at the time of use.

A translucent gel of pH 10 is obtained and this is applied for 15 minutes to a light blond head of hair containing 90% of white hair.

60 g of the composition $S_7$ are then added whilst carefully massaging the head of hair.

The pH of the dyeing mixture has then been brought down to 7 and, after a further 15 minutes, the hair is rinsed with warm water, shampooed and dried and has a final pearlescent coppery blond colouration.

EXAMPLE NO. 5

The following dyeing compositions are prepared:

| Composition $S_8$: | |
|---|---|
| 2,6-Dimethyl-5-methoxy-para-phenylenediamine | 0.96 g |
| 2-Methyl-5-N—(β-hydroxyethyl)-aminophenol | 0.35 g |
| Remcopal 334 | 25 g |
| Remcopal 349 | 20 g |
| Comperlan KD | 6 g |
| Absolute ethyl alcohol | 8 g |
| Propylene glycol | 6 g |
| Masquol DTPA | 2.4 g |
| 1-Phenyl-3-methylpyrazol-5-one | 0.2 g |
| Hydroquinone | 0.2 g |
| 35° Bé strength sodium bisulphite solution | 1 cm³ |
| 22° Bé strength ammonia solution | 10 cm³ |
| Water q.s.p. | 100 g |
| Composition $S_9$: | |
| 1-N,N—Dimethylamino-3-acetylaminobenzene | 0.35 g |
| Palmitic acid | 9 g |
| Oleic acid | 13.5 g |
| Brij 76 | 4 g |
| Propyl para-hydroxybenzoate | 0.05 g |
| Methyl para-hydroxybenzoate | 0.1 g |
| Ethylglycol | 5 g |
| 35° Bé strength sodium bisulphite solution | 1 cm³ |
| Triethanolamine | 0.3 g |
| Water q.s.p. | 100 g |

50 g of the translucent gel obtained by mixing 25 g of the composition $S_8$ with 25 g of the oxidising composition 02 are applied to a light blond head of hair containing a very high percentage of white hair.

The dyeing mixture thus has a pH of 10.

After 15 minutes, 30 g of the composition $S_9$, which lowers and buffers the pH of the dyeing mixture to about 7, are incorporated whilst slowly massaging the head of hair.

30 minutes after the start of the application, the head of hair is washed with warm water and then shampooed and is finally dried.

The masking pearlescent light blond tint obtained is substantially stronger and more attractive than that obtained when the base and the two oxidative couplers are applied simultaneously at the same concentration and in the same carrier, but either at a pH of 10 or at a pH of 7.

EXAMPLE NO. 6

The following dyeing composition is prepared:

| Composition $S_{10}$: | |
|---|---|
| 2-Methyl-5-N—acetylaminoaniline | 0.33 g |
| Palmitic acid | 9 g |
| Oleic acid | 13.5 g |
| Brij 76 | 4 g |
| Propyl para-hydroxybenzoate | 0.05 g |
| Methyl para-hydroxybenzoate | 0.1 g |
| Ethylglycol | 5 g |
| 35° Bé strength sodium bisulphite solution | 1 cc |
| Triethanolamine | 0.3 g |
| Water q.s.p. | 100 g |

80 g of the gel of pH 10 obtained by mixing equal weights of the composition $S_8$ (defined in Example 5) and the oxidising composition O2 are applied to a head of hair which has initially been dyed very light blond.

After 15 minutes, 80 g of the composition $S_{10}$, which lowers and buffers the pH of the dyeing mixture to 6.5, are added.

After 15 minutes, the hair is rinsed with water, shampooed and dried.

The highly pearlescent light blond colouration obtained is substantially stronger than that obtained when the base and the two oxidative couplers are applied simultaneously at the same concentration and in the same support, but either at a pH of 10 or at a pH of 7.

EXAMPLE NO. 7

The following dyeing composition is prepared:
Composition $S_{11}$:

This is identical to the composition of Example 6, but the 2-methyl-5-N-acetylaminoaniline has been replaced by 0.37 g of meta-ureidoaniline.

The procedure is otherwise exactly as in Example 6, using a head of hair which has initially been dyed very light blond.

At the end of the application, which is carried out in two stages and without intermediate rinsing, the head of hair is coloured pearlescent blond.

EXAMPLE NO. 8

The following dyeing compositions are prepared:

| Composition $S_{12}$: | |
|---|---|
| Para-phenylenediamine | 0.32 g |
| Remcopal 334 | 20 g |
| Remcopal 349 | 20 g |
| Carbopol 934 | 1.25 g |

-continued

| | |
|---|---|
| Ethylene glycol distearate | 0.5 g |
| Propylene glycol | 6 g |
| Absolute ethyl alcohol | 8 g |
| 35° Bé strength sodium bisulphite solution | 1 cc |
| Water q.s.p. | 100 g |
| Composition $S_{13}$: | |
| 2-Methylresorcinol | 2.5 g |
| Remcopal 334 | 22 g |
| Remcopal 349 | 22 g |
| Propylene glycol | 11 g |
| Absolute ethyl alcohol | 8 g |
| Masquol DTPA | 2.5 g |
| 35° Bé strength sodium bisulphite solution | 1 cc |
| Hydroquinone | 0.2 g |
| 1-Phenyl-3-methylpyrazol-5-one | 0.2 g |
| 22° Bé strength ammonia solution | 10 cc |
| Water q.s.p. | 100 g |

40 g of the composition $S_{12}$ of pH 5 are applied, for 15 minutes, to a blond head of hair containing a high percentage of white hair.

40 g of the gel obtained by mixing equal weights of the composition $S_{13}$ and the oxidising composition O1 are then added thereto.

The dyeing mixture of pH 10.5 gradually becomes coloured and, after 15 minutes, the head of hair is rinsed; after shampooing and drying, it is uniformly coloured golden light chestnut.

EXAMPLE NO. 9

The following dyeing compositions are prepared:

| | |
|---|---|
| Composition $S_{14}$: | |
| 1-N—(γ-Aminopropyl)-aminoanthraquinone hydrochloride | 0.065 g |
| Monoethanolamine q.s.p. | pH 7 |
| Water q.s.p. | 100 g |
| Composition $S_{15}$: | |
| 22° Bé strength ammonia solution | 20 cc |
| Water q.s.p. | 100 g |

10 g of the composition $S_{14}$ are applied, for 30 minutes, to a swatch of highly sensitised blond hair. The dissolved red dyestuff penetrates deeply into the fibres and 10 g of the composition $S_{15}$ are then added to the dyebath. The pH then rises to 12. The dyestuff precipitates in the hair and, finally, after rinsing with warm water and drying, the deep red colouration of the swatch is more intense than when the latter is treated for 35 minutes with 10 g of composition $S_{14}$ alone.

EXAMPLE NO. 10

The following dyeing compositions are prepared:

| | |
|---|---|
| Composition $S_{18}$ | |
| 1,2,4-Trihydroxybenzene | 2.5 g |
| Cellosize WP 4400 | 2 g |
| 2-Nitro-4-hydroxyaniline | 0.3 g |
| Butylglycol | 10 g |
| Ethylenediaminetetraacetic acid | 0.2 g |
| Water q.s.p. | 100 g |
| The pH is adjusted to 2.6 with phosphoric acid. | |
| Composition $S_{19}$ | |
| Cellosize WP 4400 | 2 g |
| 22° Bé strength ammonia solution | 10 cc |
| Water q.s.p. | 100 g |

A 1 g swatch of chestnut hair is immersed in 10 g of the composition $S_{18}$. After 15 minutes, 10 g of the composition $S_{19}$ are added and the mixture of pH 10 is left on the hair for a further 20 minutes.

After rinsing, shampooing and drying, the hair is coloured coppery chestnut.

EXAMPLE NO. 11

The following dyeing compositions are prepared:

| | |
|---|---|
| Composition $S_{22}$ | |
| N,N'—(p-Aminophenyl)-N,N'—(β-hydroxyethyl)-ethylenediamine dihydrochloride | 0.8 g |
| N,N'—(p-Aminophenyl)-tetramethylenediamine tetrahydrochloride | 0.4 g |
| α-Naphthol | 0.05 g |
| Resorcinol | 0.3 g |
| Remcopal 334 | 22 g |
| Remcopal 349 | 22 g |
| Propylene glycol | 11 g |
| Absolute ethyl alcohol | 8 g |
| 35° Bé strength sodium bisulphite solution | 1 cc |
| Masquol DPTA | 2.5 g |
| 1-Phenyl-3-methylpyrazol-5-one | 0.2 g |
| 22° Bé strength ammonia solution | 10 g |
| Water q.s.p. | 100 g |
| Composition $S_{23}$ | |
| N—(3-Aminophenyl)-urea hydrochloride | 0.05 g |
| 4-N—(β-hydroxyethyl)-amino-3-nitroanisole | 0.4 g |
| Remcopal 334 | 20 g |
| Remcopal 349 | 20 g |
| Carbopol 934 | 1.25 g |
| Ethylene glycol distearate | 0.5 g |
| Propylene glycol | 6 g |
| Absolute ethyl alcohol | 8 g |
| Hydrochloric acid d = 1.18 | 0.3 g |
| Water q.s.p. | 100 g |

30 g of the composition $S_{22}$ are mixed with 30 g of the oxidising composition 2 at the time of use.

The resulting gel has a pH of 10.3. It is applied to a deep blond head of hair for 15 minutes. 60 g of the composition $S_{23}$ are then incorporated, without rinsing, whilst thoroughly homogenising the whole of the dyeing mixture. The pH has been lowered to 7.5.

The hair is left for a total of 30 minutes and rinsed, shampooed and dried.

They are then coloured in an ashen blond shade.

EXAMPLE 12

The following dyeing compositions are prepared:

| | |
|---|---|
| Composition $S_{24}$ | |
| 4-Amino-N-ethyl-N'—piperidinoethylaniline dihydrochloride | 0.5 g |
| 4-Amino-N—(β-diethylsulphonamidoethyl)-aniline dihydrochloride | 0.1 g |
| 2,4-Diaminophenoxyethanol dihydrochloride | 0.02 g |
| 2,6-Diaminopyridine | 0.03 g |
| Resorcinol | 0.15 g |
| Remcopal 334 | 22 g |
| Remcopal 349 | 22 g |
| Propylene glycol | 11 g |
| Absolute ethyl alcohol | 8 g |
| 35° Bé strength sodium bisulphite solution | 1 cm³ |
| Masquol DPTA | 2.5 g |
| 1-Phenyl-3-methylpyrazol-5-one | 0.2 g |
| Hydroquinone | 0.2 g |
| 22° Bé strength ammonia solution | 10 cc |
| Water q.s.p. | 100 g |
| Composition $S_{25}$ | |
| C.I. Basic Violet 10 (C.I.45.170) | 0.3 g |
| C.I. Basic Brown (C.I.21.000) | 0.9 g |
| Remcopal 334 | 20 g |
| Remcopal 349 | 20 g |
| Carbopol 934 | 1.25 g |
| Ethylene glycol distearate | 0.5 g |

| -continued | |
|---|---|
| Propylene glycol | 6 g |
| Absolute ethyl alcohol | 8 g |
| Phosphoric acid (d = 1.71) | 0.6 g |
| Water q.s.p. | 100 g |

A composition, of pH 10.3, consisting of a mixture of 30 g of the composition $S_{24}$ with 30 g of the oxidising solution 2, is applied for 20 minutes to a head of hair which is natural or has been coloured blond.

60 g of the composition $S_{25}$ are then added and the whole is homogenised by massaging. The pH assumes a value of 7.4. The hair is rinsed, shampooed and dried after an overall application time of 30 minutes. The head of hair is then coloured very light blond with a pearlescent ashen sheen.

EXAMPLE 13

The following dyeing compositions are prepared:

| Composition $S_{26}$ | |
|---|---|
| 3-Methyl-N,N—dimethyl-para-phenylenediamine dihydrochloride | 0.4 g |
| 2-Chloro-N—(β-hydroxyethyl)-para-phenylene-diamine sulphate | 0.1 g |
| Ethyl acetylacetate | 0.1 g |
| 2,6-Dimethylphenol | 0.1 g |
| Resorcinol | 0.2 g |
| 2-Methyl-5-N—(carbamylethyl)-aminophenol | 0.05 g |
| Meta-phenylenediamine hydrochloride | 0.03 g |
| Remcopal 334 | 22 g |
| Remcopal 349 | 22 g |
| Propylene glycol | 11 g |
| Absolute ethyl alcohol | 8 g |
| 35° Bé strength sodium bisulphite solution | 1 cc |
| Masquol DPTA | 2.5 g |
| 1-Phenyl-3-methylpyrazol-5-one | 0.2 g |
| Hydroquinone | 0.2 g |
| 22° Bé strength ammonia solution | 10 cc |
| Water q.s.p. | 100 g |
| Composition $S_{27}$ | |
| 4-Amino-3-nitrophenol | 0.2 g |
| 3-Nitro-4-aminophenoxyethanol | 0.2 g |
| Coloured polymer resulting from the condensation of 20.7 mols of 1-(chloroacetylaminopropylamino)-anthraquinone with 100 secondary amine groups of the polymer obtained by condensing equimolecular amounts of adipic acid and diethylene-triamine | 0.8 g |
| Remcopal 334 | 20 g |
| Remcopal 349 | 20 g |
| Carbopol 934 | 1.25 g |
| Ethylene glycol distearate | 0.5 g |
| Propylene glycol | 6 g |
| Absolute ethyl alcohol | 8 g |
| Hydrochloric acid d = 1.18 | 0.3 g |
| Water q.s.p. | 100 g |

A mixture, produced at the time of dyeing, of 40 g of the composition $S_{26}$ with 40 g of the oxidising composition 2 is applied to blond hair. This mixture, which has a pH equal to 10.2 after an application time of 15 minutes, is modified by the incorporation of 80 g of the composition $S_{27}$, which incorporation causes the lowering of the pH to a value of 6.7.

After a further 15 minutes, corresponding to the application time of the whole of the new dyeing mixture, the head of hair is rinsed, shampooed and dried. After this dyeing, the hair is dyed in a very light blond shade with a slight golden sheen.

EXAMPLE 14

The following dyeing compositions are prepared:

| Composition $S_{28}$ | |
|---|---|
| Remcopal 334 | 22 g |
| Remcopal 349 | 22 g |
| Propylene glycol | 11 g |
| Absolute ethyl alcohol | 8 g |
| 35° Bé strength sodium bisulphite solution | 1 cc |
| Masquol DPTA | 2.5 g |
| 22° Bé strength ammonia solution | 10 cc |
| Water q.s.p. | 100 g |
| Composition $S_{29}$ | |
| C.I. Basic Violet 1 (C.I.42.535) | 0.8 g |
| Remcopal 334 | 20 g |
| Remcopal 349 | 20 g |
| Carbopol 934 | 1.25 g |
| Ethylene glycol distearate | 0.5 g |
| Propylene glycol | 6 g |
| Absolute ethyl alcohol | 8 g |
| Phosphoric acid (d = 1.71) | 0.6 g |
| Maleic acid | 3.5 g |
| Water q.s.p. | 100 g |

60 g of a mixture, of pH 10.4, consisting of 30 g of the composition $S_{28}$ with 30 g of the oxidising composition 1 can be applied to a chestnut head of hair. It is left to act for 15 minutes, 60 g of the composition $S_{29}$ are then added, without intermediate rinsing, this bringing the pH down to 5.5, and the whole is left to act for a further 15 minutes. The hair is rinsed, shampooed and dried. It is then embellished with a slight purple-violet sheen.

EXAMPLE 15

The following dyeing compositions are prepared:

| Composition $S_{30}$ | |
|---|---|
| C.I. Basic Orange 14 (C.I.46.005) | 0.2 g |
| Coloured polymer resulting from the condensation of 21.8 mols of 2-(β-chloroacetylaminoethylamino)-anthraquinone with 100 secondary amine groups of the polymer obtained by condensing equimolecular amounts of adipic acid and diethylenetriamine | 0.3 g |
| Coloured polymer resulting from the condensation of 27.5 mols of 4-methylamino-3-nitroaniline with 100 azetidinium groups of the polymer obtained by condensing equimolecular amounts of epichlorohydrin with the polyaminoamide resulting from the condensation of equimolecular amounts of adipic acid and diethylenetriamine | 0.04 g |
| Remcopal 334 | 20 g |
| Remcopal 349 | 20 g |
| Carbopol 934 | 1.25 g |
| Ethylene glycol distearate | 0.5 g |
| Propylene glycol | 6 g |
| Absolute ethyl alcohol | 8 g |
| Phosphoric acid (d = 1.71) | 0.6 g |
| Maleic acid | 3.5 g |
| Water q.s.p. | 100 g |

The composition, of pH 10.4, consisting of a mixture of 40 g of the composition $S_{28}$ with 40 g of the oxidising composition 1 is applied for 15 minutes to a head of hair which is natural or has been coloured blond. 80 g of the composition $S_{30}$ are then incorporated, without intermediate rinsing, and this has the consequence of lowering the pH to a value of 5.4. The head of hair is massaged carefully. After an overall application time of 30 minutes, the hair is rinsed. After shampooing and drying, the shade obtained is a very light blond with a golden sheen.

EXAMPLE 16

The following dyeing composition is prepared:

| Composition S₃₁ | |
|---|---|
| C.I. Acid Red 277 | 1 g |
| Remcopal 334 | 20 g |
| Remcopal 349 | 20 g |
| Carbopol 934 | 1.25 g |
| Ethylene glycol distearate | 0.5 g |
| Propylene glycol | 6 g |
| Absolute ethyl alcohol | 8 g |
| Phosphoric acid (d = 1.71) | 0.6 g |
| Maleic acid | 3.5 g |
| Water q.s.p. | 100 g |

40 g of the composition S₂₈, mixed, before use, with 40 g of the oxidising composition 1, are applied to light blond hair. The pH of the whole is 10.4.

After an application time of 15 minutes, 80 g of the composition S₃₁ are added without rinsing. The pH has been brought down to 5.6.

After a further application time of 15 minutes, the hair is rinsed with warm water, shampooed and dried and has a final iridescent light blond colouration.

EXAMPLE 17

The following dyeing compositions are prepared:

| Composition S₃₂ | |
|---|---|
| 2,6-Dimethyl-5-methoxy-para-phenylene-diamine dihydrochloride | 0.7 g |
| Remcopal 334 | 20 g |
| Remcopal 349 | 20 g |
| Carbopol 934 | 1.25 g |
| Ethylene glycol distearate | 0.5 g |
| Propylene glycol | 6 g |
| Absolute ethyl alcohol | 8 g |
| 35° Bé strength sodium bisulphite solution | 1 cc |
| Water q.s.p. | 100 g |
| Composition S₃₃ | |
| Resorcinol | 0.3 g |
| 2,4-Diaminoanisole sulphate | 0.15 g |
| Meta-aminophenol | 0.15 g |
| Remcopal 334 | 22 g |
| Remcopal 349 | 22 g |
| Propylene glycol | 11 g |
| Absolute ethyl alcohol | 8 g |
| Masquol DPTA | 2.5 g |
| 35° Bé strength sodium bisulphite solution | 1 cc |
| Hydroquinone | 0.2 g |
| 1-Phenyl-3-methylpyrazol-5-one | 0.2 g |
| 22° Bé strength ammonia solution | 10 cc |
| Water q.s.p. | 100 g |

6 g of the composition S₃₂, the pH of which is 2.7, are applied for 15 minutes to a head of hair which is naturally coloured light blond.

A mixture, produced at the time of use, composed of 30 g of the composition S₃₃ and 30 g of the oxidising composition 1 is then added, without rinsing. The pH rises and reaches 9.3.

After a further application time of 15 minutes, the head of hair is rinsed copiously. After shampooing and drying, the hair is coloured ashen light blond.

EXAMPLE 18

The following dyeing compositions are prepared:

| Composition S₃₄ | |
|---|---|
| 2,6-Dimethyl-para-phenylenediamine dihydrochloride | 0.4 g |
| 1-Dimethylamino-3-acetylaminobenzene | 0.3 g |
| Remcopal 334 | 20 g |
| Remcopal 349 | 20 g |
| Carbopol 934 | 1.25 g |
| Ethylene glycol distearate | 0.5 g |
| Propylene glycol | 6 g |
| Absolute ethyl alcohol | 8 g |
| 35° Bé strength sodium bisulphite solution | 1 cc |
| Masquol DPTA | 2.5 g |
| Water q.s.p. | 100 g |
| Composition S₃₅ | |
| Resorcinol | 0.15 g |
| 4-Nitro-ortho-phenylenediamine | 0.3 g |
| Remcopal 334 | 22 g |
| Remcopal 349 | 22 g |
| Propylene glycol | 11 g |
| Absolute ethyl alcohol | 8 g |
| 35° Bé strength sodium bisulphite solution | 1 cc |
| Hydroquinone | 0.2 g |
| 1-Phenyl-3-methylpyrazol-5-one | 0.2 g |
| Ammonia solution | 10 cc |
| Water q.s.p. | 100 g |

60 g of the composition S₃₄ are mixed with 30 g of the oxidising composition 1 at the time of use. The pH of the mixture is 4. The composition thus obtained is applied to a blond head of hair for 15 minutes.

After these 15 minutes, 30 g of the composition S₃₅ are incorporated, without rinsing. The head of hair is massaged carefully. The pH increases and reaches 10.1.

The hair is left for a further 15 minutes. It is rinsed, shampooed and dried. The hair is then coloured very light blond with a golden sheen.

EXAMPLE 19

The following dyeing compositions are prepared:

| Composition S₃₆ | |
|---|---|
| 1,2,4-Trihydroxybenzene | 2.5 g |
| 3-Nitro-4-(β-hydroxyethylamino)-phenol | 0.3 g |
| Ethylcellosolve | 1 g |
| Hydroxyethylcellulose sold under the name Cellosize WP 3 by Messrs. Carbide and Carbon | 3.3 g |
| 35° Bé strength sodium bisulphite solution | 1 cc |
| Ethylenediaminetetraacetic acid | 0.1 g |
| Tartaric acid q.s.p. | pH 3 |
| Water q.s.p. | 100 g |
| Composition S₃₇ | |
| Hydroxyethylcellulose sold under the name Cellosize WP 3 by Messrs. Carbide and Carbon | 3.3 g |
| 22° Bé strength ammonia solution | 10 cc |
| Water q.s.p. | 100 g |

50 g of the composition S₃₆ are applied to a chestnut head of hair. The pH of this composition is 3. After 15 minutes, 50 g of the composition S₃₇ are added, without rinsing, and this increases the pH to 10; after 15 minutes, the hair is rinsed, shampooed and dried. The head of hair is then dyed in a mahogany chestnut shade.

EXAMPLE 20

The following dyeing compositions are prepared:

| Composition S₃₈ | |
|---|---|
| C.I. Basic Violet 1 (C.I.42.535) | 2 g |
| Monoethanolamine q.s.p. | pH 7 |
| Water q.s.p. | 100 g |
| Composition S₃₉ | |
| 22° Bé strength ammonia solution | 20 cc |
| Water q.s.p. | 100 g |

50 g of the composition S38, of pH 7, are applied to a deep chestnut head of hair. After leaving the hair for 30 minutes, 50 g of the composition S39 are added, without intermediate rinsing. The pH then increases to a value of 11.7. The dyestuff precipitates inside the hair. After rinsing and drying, the head of hair exhibits an intense purple-violet sheen.

EXAMPLE 21

The following dyeing composition is prepared:

| Composition S40 | |
| --- | --- |
| C.I. Basic Orange 14 (C.I.46.005) | 2 g |
| Monoethanolamine q.s.p. | pH 7 |
| Water q.s.p. | 100 g |

40 g of the composition S40, of pH equal to 7, are applied to a deep blond head of hair. After an application time of 30 minutes, 40 g of the composition S39 are added, without rinsing. The pH reaches about 12 and the dyestuff precipitates in the hair.

After about 5 minutes, the hair is rinsed and dried.

The hair is dyed in a blond shade with an intense coppery sheen.

We claim:

1. Process for dyeing keratin fibres, which comprises treating the fibres with a first composition having a pH from 7 to 13, and subsequently, without any intermediate rinsing, treating the said fibres with a second composition having a pH which is less than 8 which contains a direct dyestuff which is a nitrobenzene dyestuff, anthraquinone dyestuff, triphenylmethane dyestuff, azo dyestuff, metallised dyestuff, xanthene dyestuff, acridine dyestuff or a polymeric dyestuff of the formula

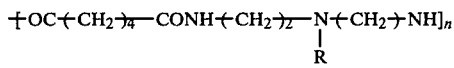

wherein R represents H or an anthraquinone dyestuff and n represents an integer from 2 to 20 and mixtures thereof.

2. Process according to claim 1, in which the first composition contains an oxidative dyestuff selected from the group consisting of an oxidative dyestuff precursor of the para or ortho type; a mixture of an oxidative dyestuff of the ortho or para type and a coupler; a diphenylamine; and mixtures thereof.

3. Process according to claim 2, in which the oxidative dyestuff precursor of the para type is selected from the group consisting of a para-aminophenol, and N,N'-diarylalkylenediamine in which the aryl groups are substituted in the para position by OH or an amino group wherein the amino group is unsubstituted or substituted by an alkyl group, wherein the aryl groups are independently unsubstituted, alkyl-substituted or halogen-substituted, and in which the alkylene group contains a chain hetero-atom of oxygen or nitrogen, and is unsubstituted or hydroxy-substituted or alkyl-substituted, the nitrogen atoms of the alkylenediamine group being unsubstituted, alkyl-substituted, hydroxyalkyl-substituted or aminoalkyl-substituted.

4. Process according to claim 2, in which the oxidative dyestuff precursor of the para type is a compound of the formula:

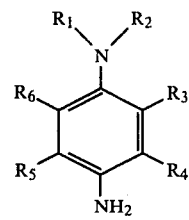

in which: R1 and R2 independently of one another denote hydrogen, phenyl, furfuryl, tetrahydrofurfuryl or a linear or branched alkyl group which is unsubstituted or chain-terminated by a hydroxyl, alkoxy, a primary, secondary or tertiary amino group, acylamino, alkyl or aryl-sulphonylamino, carbalkoxyamino, ureido, carboxyl or carbamyl in which the nitrogen atom is unsubstituted or mono- or di-substituted, said alkyl groups including alkyl groups containing oxygen or nitrogen atoms and alkyl groups substituted by hydroxy or amino groups; or R1 and R2 together form, together with the nitrogen atom to which they are attached, a heterocyclic ring; and R3, R4, R5 and R6 independently of one another denote hydrogen, halogen, linear or branched alkyl which is unsubstituted or substituted by one or more OH, amino or alkoxy groups, or a group OZ, Z denoting alkyl, hydroxyalkyl, alkoxyalkyl, acylaminoalkyl, carbalkoxyaminoalkyl, mesylaminoalkyl, ureidoalkyl, aminoalkyl or mono- or di-alkylaminoalkyl, the alkyl radicals containing 1 to 6 carbon atoms, with the proviso that if R2 denotes phenyl, R1, R3, R4, R5 and R6 denote hydrogen, and that if R1 and R2 are both different from hydrogen, R3 and R6 both denote hydrogen or an organic or inorganic acid salt thereof.

5. Process according to claim 1, in which the first composition contains an oxidative dyestuff precursor and the second composition contains a coupler of the formula:

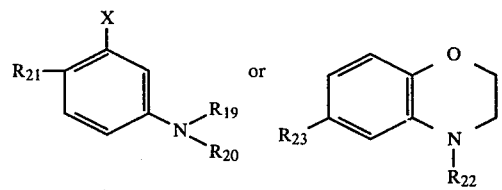

in which: X denotes —OH, —NH2 or —N(CH3)2, R21 or R19 denotes H or an alkyl radical having 1 to 4 carbon atoms, R20 denotes COCH3, CONH2 or an alkyl radical having 1 to 4 carbon atoms, R22 denotes hydrogen, —COCH3 or —CONH2, and R23 denotes OH or amino, or an organic or inorganic acid salt thereof, or 6-aminoindoline; and mixture thereof.

6. Process according to claim 1 in which the second composition is acidic.

7. Process for dyeing keratin fibres which comprises:
(a) treating the fibres with a first composition which has a pH from 7 to 13 and contains an oxidative dyestuff precursor of the para type selected from the group consisting of:
a para-aminophenol;
N,N'-diarylalkylenediamine in which the aryl groups are substituted in the para position by OH or an amino group wherein the amino group is unsubstituted or substituted by an alkyl group, wherein the aryl groups are independently unsubstituted, alkyl-substituted or halogen-substituted, and in which the alkylene group contains a chain hetero-atom of oxygen or nitrogen, and is unsubstituted or hydroxy-substituted or alkyl-substituted, the nitrogen atoms of the alkylenediamine group being unsubstituted, alkyl-substituted, hydroxyalkyl-substituted or aminoalkyl-substituted; and a compound of the formula:

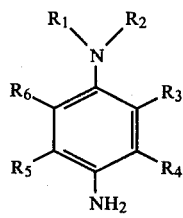

in which: $R_1$ and $R_2$ independently of one another denote hydrogen, phenyl, furfuryl, tetrahydrofurfuryl or a linear or branched alkyl group which is unsubstituted or chain-terminated by a hydroxyl, alkoxy, a primary, secondary or tertiary amino group, acylamino, alkyl or aryl-sulphonyl-amino, carbalkoxyamino, ureido, carboxyl or carbamyl in which the nitrogen atom is unsubstituted or mono- or di-substituted, said alkyl groups including alkyl groups containing oxygen or nitrogen atoms and alkyl groups substituted by hydroxy or amino groups; or $R_1$ and $R_2$ together form, together with the nitrogen atom to which they are attached, a heterocyclic ring; and $R_3$, $R_4$, $R_5$ and $R_6$ independently of one another denote hydrogen, halogen, linear or branched alkyl which is unsubstituted or substituted by one or more OH, amino or alkoxy groups, or a group OZ, Z denoting alkyl, hydroxyalkyl, alkoxyalkyl, acylaminoalkyl, carbalkoxyaminoalkyl, mesylaminoalkyl, ureidoalkyl, aminoalkyl or mono- or di-alkylaminoalkyl, the alkyl radicals containing 1 to 6 carbon atoms, with the proviso that if $R_2$ denotes phenyl, $R_1$, $R_3$, $R_4$, $R_5$ and $R_6$ denote hydrogen, and that if $R_1$ and $R_2$ are both different from hydrogen, $R_3$ and $R_6$ both denote hydrogen or an organic or inorganic acid salt thereof; and mixture thereof; and (b) subsequently, without any intermediate rinsing, treating the said fibres with a second composition which has an acid pH and contains a coupler of the formula:

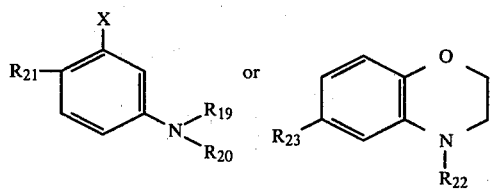

in which: X denotes —OH, —NH$_2$ or —N(CH$_3$)$_2$, $R_{21}$ or $R_{19}$ denotes H or an alkyl radical having 1 to 4 carbon atoms, $R_{20}$ denotes COCH$_3$, CONH$_2$ or an alkyl radical having 1 to 4 carbon atoms, $R_{22}$ denotes hydrogen, —COCH$_3$ or —CONH$_2$, and $R_{23}$ denotes OH or amino, or an organic or inorganic acid salt thereof, or 6-aminoindoline.

8. Process according to claim 1 or 7, in which the first composition is mixed with an oxidising agent or composition just before use.

9. Process according to claim 2 or 7, in which the dyestuff precursor or coupler is present in the composition in an amount from 0.005 to 10% by weight.

10. Process according to claim 2 or 7, in which the dyestuff precursor or coupler is present in the composition in an amount from 0.01 to 5% by weight.

11. Process for dyeing keratin fibres which comprises treating the fibres with a first composition having a pH of less than 8, and containing an oxidative dyestuff amine-substituted aromatic precursor of the para type, in which either the amino group is secondary or tertiary, or the amino group is primary and the aromatic nucleus carries at least 2 substituents and subsequently, without any intermediate rinsing, treating the said fibres with a second composition having a pH so as to give on the keratin fibres a pH of more than 8.

12. Process for dyeing keratin fibres, which comprises treating the fibres with a first composition having a pH of less than 8 and containing a direct dyestuff; said direct dyestuff being a nitrobenzene dyestuff, anthraquinone dyestuff, triphenylmethane dyestuff, azo dyestuff, metallized dyestuff, xanthene dyestuff, acridine dyestuff or a polymeric dyestuff of the formula

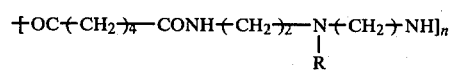

wherein R represents H or an anthraquinone dyestuff and n represents a integer from 2 to 20, and mixtures thereof; wherein said direct dyestuff precipitates on the fibres after treating the fibres; and without intermediate rinsing, treating the fibres treated with the first composition with a second composition having a pH of more than 8.

13. Process according to claim 12 in which the direct dyestuff is an anthraquinone dyestuff, a nitrobenzene dyestuff, a triphenylmethane dyestuff, an azo dyestuff, a metallised dyestuff, a xanthene dyestuff, an acridine dyestuff or a polymeric dyestuff selected from an anthraquinone dyestuff grafted on a polymer and a nitrobenzene dyestuff grafted on a polymer wherein the polymer is a product of the polycondensation of adipic acid and diethylene triamine.

14. Process according to claim 1 or 12 in which the direct dyestuff is present in the composition in an amount from 0.005 to 10% by weight.

15. Process according to claim 1 or 12 in which direct dyestuff is present in the composition in an amount from 0.05 to 6% by weight.

16. Process according to any one of claims 11, 12, or 13, in which the first composition contains a rapid oxidative dyestuff selected from the group consisting of a polyhydroxybenzene; polyhydroxynaphthalene; polyaminobenzene; polyaminophenol; polyamino-polyhydroxybenzene; and a polyhydroxy- or polyaminohydroxy-indole.

17. Process according to any one of claims 11, 12, or 13 in which the first composition contains a rapid oxidative dyestuff selected from the group consisting of a polyhydroxybenzene; polyaminobenzene; polyaminophenol; polyamino-polyhydroxybenzene; and a polyhydroxy- or polyaminohydroxy-indole.

18. Process according to any one of claims 11, 12, or 13, in which the first composition contains a diphenylamine.

19. Process according to any one of claims 11, 12, or 13 in which the second composition contains an oxidative dyestuff of the para type.

20. Process according to any one of claims 1, 7, 11 or 12 in which the composition which is alkaline contains an alkalising agent which is sodium hydroxide, ammonia, potassium hydroxide, piperidine, an alkylamine, an alkanolamine, an alkylalkanolamine, sodium carbonate, potassium carbonate or ammonium carbonate.

21. Process according to any one of claims 1, 7, 11 or 12 in which the composition which is acidic contains an acidifying agent which is hydrochloric acid, sulphuric acid, boric acid, phosphoric acid, formic acid, acetic acid, propionic acid, butyric acid, pentanoic acid, hexanoic acid, heptanoic acid, octanoic acid, cinnamic acid, lactic acid, glycolic acid, caproic acid, valeric acid, stearic acid, oleic acid, ricinoleic acid, linoleic acid, palmitic acid, lauric acid, myristic acid, oxalic acid, malonic acid, succinic acid, glutamic acid, adipic acid, maleic acid, fumaric acid, tartaric acid, malic acid or citric acid.

22. Process according to any one of claims 1, 7, 11 or 12, in which the pH of the composition is adjusted with an acidifying or alkalising agent present in an amount from 0.05 to 25% by weight.

23. Process according to any one of claims 1, 7, 11 or 12, in which the pH of the composition is adjusted with an acidifying or alkalising agent in an amount from 0.2 to 10% by weight.

24. Process according to any one of claims 1, 7, 11 or 12, in which the first composition is applied for 2 to 40 minutes and the second composition is applied for 1 to 40 minutes.

25. Process according to any one of claims 1, 7, 11 or 12, in which the composition are in the form of aqueous composition, thickened composition, gelled or gellable compositions, creams, or are packaged in an aerosol.

26. Process according to any one of claims 1, 7, 11 or 12 for dyeing human hair.

27. The process of claim 2, wherein the oxidative dyestuff precursor of the para type is para-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol or N-methyl-para-aminophenol.

28. The process according to claim 2, in which the oxidative dyestuff precursor of the para type is 2,5-diaminopyridine, 2-dimethylamino-5-aminopyridine or 2-diethylamino-5-aminopyridine.

29. Process according to claim 2, in which the oxidative dyestuff precursor of the para type is 2-methyl-6-aminobenzomorpholine.

30. Process according to claim 2, in which the oxidative dyestuff precurser of the para type is 5-aminoindole.

31. Process according to claim 2 in which the coupler is selected from α-naphthol, 2,6-diaminopyridine, 6-hydroxybenzo-morpholine, 6-aminobenzo-morpholine and pyrazolone.

* * * * *